US 9,958,187 B2

(12) United States Patent
Monroy

(10) Patent No.: US 9,958,187 B2
(45) Date of Patent: May 1, 2018

(54) ACTIVE COOLING SYSTEM FOR TRANSPORT OF BODY FLUIDS AND ORGANS

(71) Applicant: Jerry Monroy, Houston, TX (US)

(72) Inventor: Jerry Monroy, Houston, TX (US)

( * ) Notice: Subject to any disclaimer, the term of this patent is extended or adjusted under 35 U.S.C. 154(b) by 138 days.

(21) Appl. No.: 14/887,525

(22) Filed: Oct. 20, 2015

(65) Prior Publication Data

US 2017/0108253 A1  Apr. 20, 2017

(51) Int. Cl.
*F25B 21/02* (2006.01)
*A01N 1/00* (2006.01)
*F25D 11/00* (2006.01)

(52) U.S. Cl.
CPC ............... *F25B 21/02* (2013.01); *A01N 1/00* (2013.01); *F25D 11/00* (2013.01); *F25B 2321/0212* (2013.01); *F25B 2600/07* (2013.01); *F25D 2700/12* (2013.01)

(58) Field of Classification Search
CPC .............................. F25B 21/02; F25B 21/04
USPC .................... 62/3.2, 3.3, 3.6, 457.1
See application file for complete search history.

(56) References Cited

U.S. PATENT DOCUMENTS

2008/0300660 A1* 12/2008 John ................. A61N 1/3785
607/61
2011/0121654 A1* 5/2011 Recker ................ H02J 9/065
307/66
2012/0304866 A1* 12/2012 Barrett ................ B01D 53/74
96/244

* cited by examiner

*Primary Examiner* — Melvin Jones
(74) *Attorney, Agent, or Firm* — The Petruzzi Law Firm; James D. Petruzzi

(57) ABSTRACT

An active cooler having an insulated five sided box having an inner chamber, the box has an openable lid hingedly attached to the upper edge of the box, a temperature sensor in the inner chamber for detecting temperature readings of the inner chamber when the lid is closed, a peltier cooling element operably engaged to the inner chamber to remove heat, a voltage regulator operably connected to the sensor to change the cooling element in response to temperature readings from the sensor, and a wireless transmitter connected to the temperature sensor for transmission of temperature readings and detection of pre-determined temperatures. The cooler may also have a program that is operated by an onboard computer to generate temperature and time related data, transmit the data via cell phone, internet, or local area and interact with hand held devices via specialized application software.

20 Claims, 3 Drawing Sheets

ACTIVE COOLING SYSTEM FOR TRANSPORT OF BODY FLUIDS AND ORGANS

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

Field of the Invention

This invention relates generally to the field of coolers and more particularly to an active cooling system for transport of body fluids and organs.

Description of Related Art

Blood products, tissues, and/or organs, must be maintained at a narrow temperature range in order to ensure viability. Temperatures less than 0° Celsius will damage these products due to the intracellular crystallization of water. Elevated temperatures increase the risk of bacterial proliferation causing life-threatening transfusion reactions such as septic shock and even death. It is therefore imperative that such products be maintained at a storage temperature of 1-6° Celsius and transport temperatures of 1-10° Celsius. While there are insulated box systems designed to maintain these products in a cool environment, there is no product on the market that will constantly monitor the temperature ensuring this parameter is maintained.

HemoTemp® II stickers have been used to determine if the blood product was out of the acceptable temperature range during transport. If the product was out of temperature, it is not used and ultimately wasted. While this may prevent adverse results from the inadvertent transfusion of an "out-of-temp" blood product or organ, it results in a costly waste of an expensive and precious resource.

The present invention overcomes these problems through use of an innovative combination of an electronically monitored cooling system that maintains a constant temperature within acceptable ranges, monitors temperature changes, and advises the use of any deviation from the pre-determined temperature range to prevent harmful swings in temperatures. The present invention may be used for organs and other tissue may be used for anything perishable and/or requiring temperature/humidity controlled environment including pharmaceuticals and foodstuffs.

BRIEF SUMMARY OF THE INVENTION

In accordance with a preferred embodiment of the present invention, there is shown an active cooler having an insulated five sided box having an inner chamber, the box has an openable lid hingedly attached to the upper edge of the box, a temperature sensor in the inner chamber for detecting temperature readings of the inner chamber when the lid is closed, a peltier cooling element operably engaged to the inner chamber to remove heat, a voltage regulator operably connected to the sensor to change the cooling element in response to temperature readings from the sensor, and a wireless transmitter connected to the temperature sensor for transmission of temperature readings and detection of pre-determined temperatures.

In accordance with another preferred embodiment of the invention, there is shown an active cooler having an insulated five sided box having an inner chamber, the box has an openable lid hingedly attached to the upper edge of the box, a temperature sensor in the inner chamber for detecting temperature readings of the inner chamber when the lid is closed, a peltier cooling element operably engaged to the inner chamber to remove heat, a voltage regulator operably connected to the sensor to change the cooling element in response to temperature readings from the sensor, and a wireless transmitter connected to the temperature sensor for transmission of temperature readings and detection of pre-determined temperatures.

In accordance with another preferred embodiment of the invention, there is shown an active cooler having an insulated container having an openable lid, the container having an inner chamber, a temperature sensor in the inner chamber for detecting temperature readings of the inner chamber when the lid is closed, a peltier cooling element operably engaged to the inner chamber to remove heat, a voltage regulator operably connected to the sensor to change the cooling element in response to temperature readings from the sensor, and a wireless transmitter connected to the temperature sensor for transmission of temperature readings and detection of pre-determined temperatures.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for later filed claims and as a representative basis for teaching one skilled in the art to employ the present invention in virtually any appropriately detailed system, structure or manner.

The present invention includes an active-cooling solution that constantly monitors the environment and presenting alarms when temperatures are approaching unacceptable levels. This provides time to act and prevent damage and wastage saving the product that can often cost thousands of dollars per unit of blood, and in the case of an organ, priceless.

Currently, there are no regulations by the certifying agencies, AABB, CAP, or FDA, describing effective transport of these products using a persistent monitoring system. This is likely due to the unavailability of a reliable, testable, and feasible system.

The present invention persistently monitors for not just transport, but for prolonged storage of product(s) at the bedside. This system provides caretakers with bedside access to blood products for immediate transfusion of critically ill patients, safe extended storage for lengthy operating procedures, printable temperature data logs for the duration of storage in order to meet the stringent quality assurance requirements of all regulatory agencies, and integrated alarm system(s) in order to prevent the loss of product.

Portable cooling is provided by a powered thermo-electric peltier effect system. This system allows fast cooling, lightweight, and reliability. Monitoring is provided by an integrated temperature monitor with alarm and Wi-Fi connectivity for direct 24/7 monitoring by a centralized networked computer system. The monitor will provide feedback to a voltage regulator in order to insure the cooler is maintained at the appropriate temperature. Currently, the monitor provides a downloadable, detailed profile of the temperature environment along with a constant graph curve.

Figure 1:
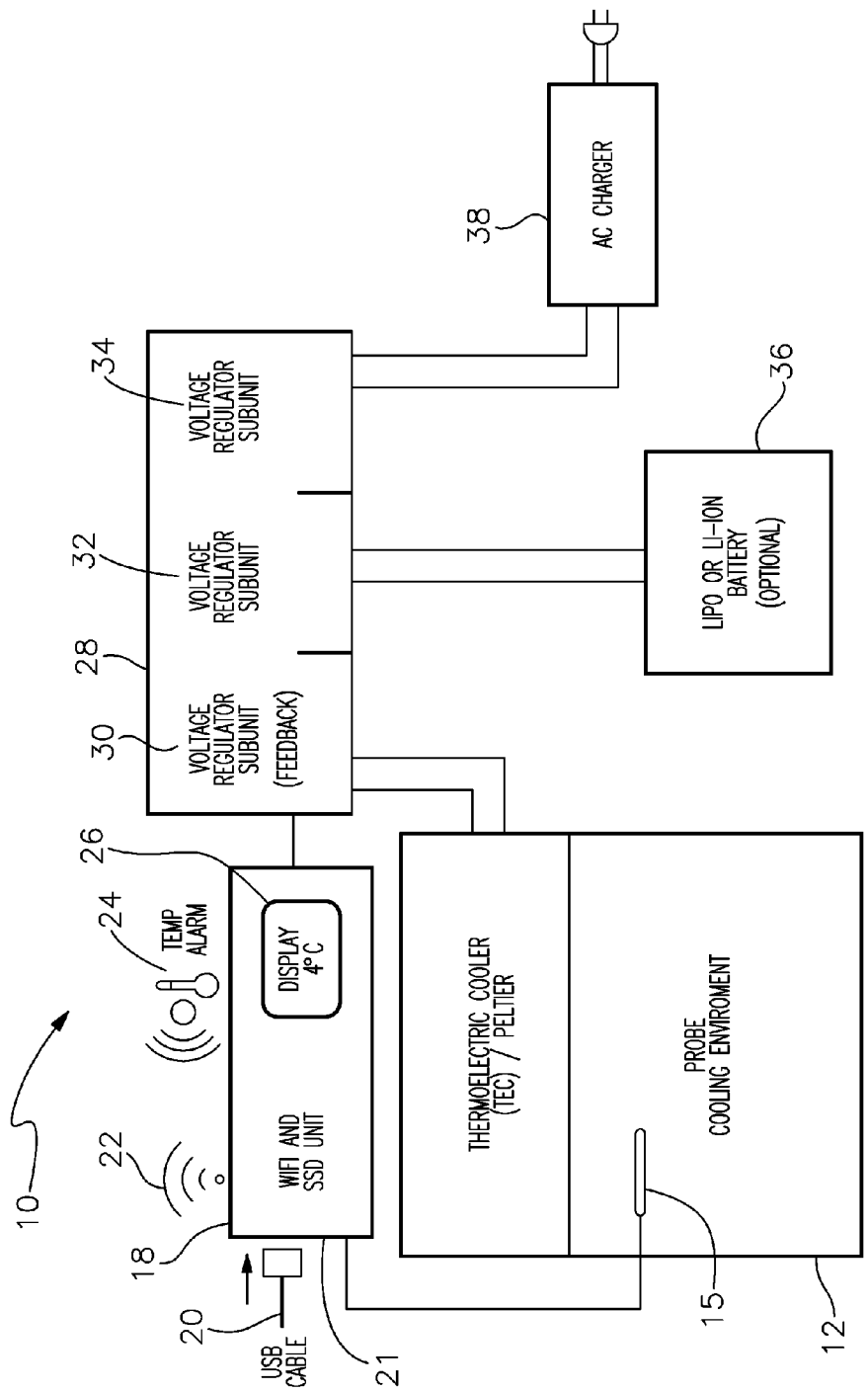
FIG. 1 shows a schematic diagram of an active cooler according to a preferred embodiment of the invention.

Turning now to FIG. 1, there is shown a schematic of a cooling system according to a preferred embodiment of the invention. FIG. 1 shows active cooler 10 composed of a cooler box 12, having probe cooling environment 14, and thermoelectric cooler 16. Thermoelectric cooler 16 is preferably a peltier style cooling element. Active cooler 10 also has a WiFi (wireless transmitter) and or SSD (solid state disc) unit 18, having wireless out signal 22, alarm display 26, and temperature alarm signal 24. WiFi and SSD unit 18 also has conventional USB access 21 that permits computer access to WiFi and SSD unit 18 through USB cable 20. Display 26 may preferably have a backup battery and lights such as LED's that activate responsive to appropriate signaling.

Active cooler 10 has a thermoelectric cooler 16 connected to input and output wires 17 and 19 to allow electronic signal transmission from the Power subunit 28. Power subunit 28 has voltage regulator feedback 30, voltage regulator 32 for controlling an external battery 36 or for controlling AC charger 38. External battery 36 may be of any of a variety of configurations, preferably a lithium-ion polymer battery (LiPO) or a lithium-ion battery (Li-ion) style battery.

In operation, probe 15 is placed in operable engagement with probe cooling environment 14 to sense actual temperature. Probe cooling environment 14 is preferably a closed chamber with lid more fully described in connection with FIG. 3. Cooling probe 15 sends electronic signals representative of the temperature to the WiFi and SSD unit 18 and in turn into the voltage feedback unit 30 and voltage regulator unit 32. As temperature variances are detected, the feedback loop signals through input and output lines 17 and 19 to the thermoelectric cooler to increase or decrease cooling to maintain the temperature at a narrow range. Preferably temperatures are maintained between 1-6° Celsius for storage and between 1-10° Celsius for transport. By using a thermoelectric peltier element, the temperature can be maintained within fine tolerances over long periods of time.

WiFi and SSD unit 18 is capable of showing the interior temperature of the cooler at display 26, and sending a temperature alarm 24 via WiFi or other communication systems including cell phones, internet, and Local Area Network. Such monitoring by alarm and WiFi connectivity permits 24 hour, seven day a week monitoring by remote users through a centralized networked computer system. This allows hospital services such as transfusion services, transplant services, pharmaceutical transport and any other temperature sensitive transporting to be accomplished while being constantly monitored through wireless signals and alarms to anyone with access to the system.

Figure 2:
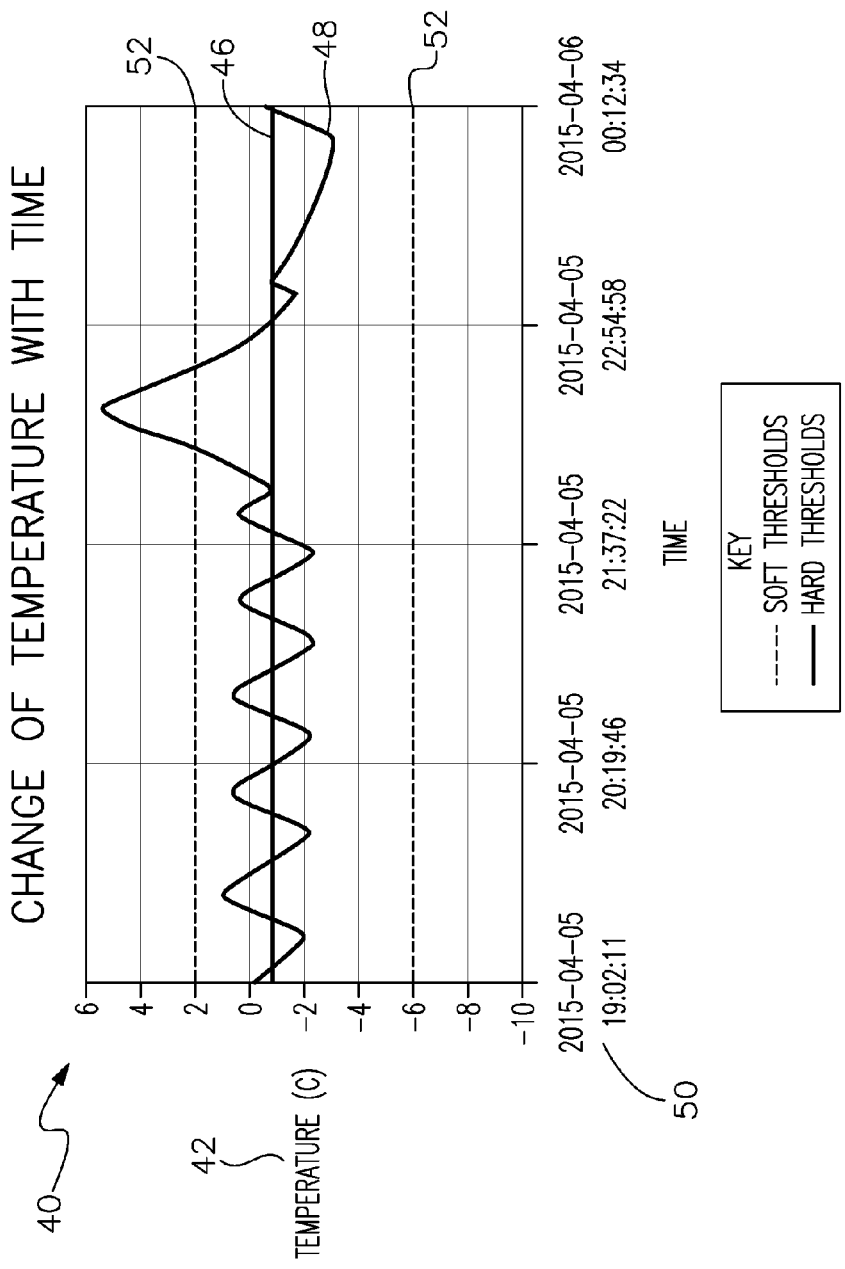
FIG. 2 shows a graph of temperature readings for an active cooler according to a preferred embodiment of the invention.

FIG. 2 shows a sample temperature graph of the internal cooling environment of a cooler according to a preferred embodiment of the invention. As can be readily understood, monitoring of temperature is important to maintain the viability of the transported item, whether it be blood, organs, or other materials that are temperature sensitive. But it also permits data collection to provide a kind of verification stamp that shows the item maintained the proper temperature throughout its transport sequence, and not just a proper temperature upon arrival or when being sent. FIG. 2 shows a sample graph of data 40, with vertical axis 42 for temperature, and horizontal axis 44 for time. Time stamps 50 are stored in the data collection and relayed through the WiFi and or stored onboard memory (not shown) for different time increments and dates. Hard threshold 46 depicts a temperature ideal for the particular item with allowed soft threshold 52 reflecting a minimum and maximum allowable temperature for the item while being stored in the active cooler. Sensed data line 48 shows the actual sensed temperatures during the sample period in this case from 19:02:11 on Apr. 5, 2015 until 00:12:34 on Apr. 6, 2015. This data is constantly being recorded and uploaded via USB or WiFi Signal to the central computer system, and/or remote systems including cellular phones such as the I-Phone.

By maintaining this data during the entire transport sequence, the transporter knows that the temperature is being maintained appropriately and can demonstrate to the end use the history of temperatures to show the item was maintained at the correct temperature. Similarly, if the temperature falls out of tolerance, signals may be sent to any of the aforementioned monitoring systems, including computers and cell phones to provide immediate notification that may require additional steps. Importantly, the data collection graph of FIG. 2 may be shown to the end users to demonstrate organ providence and proper control over the item to ensure viability for end use.

Figure 3:
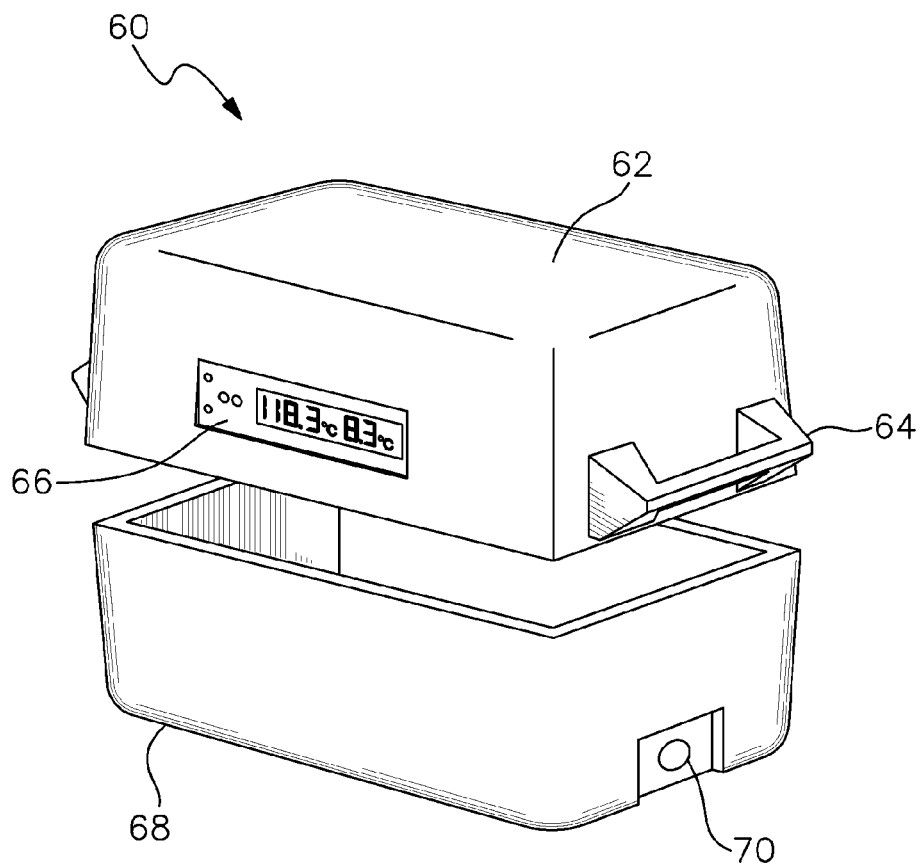
FIG. 3 shows a perspective view of an active cooler according to a preferred embodiment of the invention.

FIG. 3 shows a cooler according to a preferred embodiment of the invention. Cooler 60 may be of any variety of materials utilizing insulated wall construction, typically with an upper moveable lid 62, and lower chamber 68 for storage. Handles 64 may be placed on both side of cooler 60 for easy transport and handling. On the face of lid 62 may be placed a digital system that is programmable, has a USB downloadable port, and includes WiFi and SSD unit 18, with display 26 as previously described. Chamber 68 is configured for storing and transporting blood packets, organs, pharmaceuticals, and any other material or item for which temperature control is desired within very narrow ranges and that requires constant monitoring an updating. Lid 62 may have an autolocking feature when temperature exceeds pre-set limits to prevent usage of the item without further evaluation. This prevents the use of an organ, blood or other item that fell out of tolerance during transport but otherwise appears to be in range when delivered.

Cooler 60 also has exhaust fan 70 that may be comprised of one or more fans to regulate temperature along with the operation of thermoelectric cooler 16. Fan unit 70 is operably connected to temperature sensor probe 15 and thermoelectric cooler 16 and upon appropriate electronic signal may vent cooled air outside chamber 68 to increase temperature as needed. Fan 70 is also used to intake warmer external air as needed to effect the appropriate temperature. Fan 70 may also be employed to provide fresh air if needed in a particular application.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the later issued claims.

I claim:

1. An active cooler comprising:
   an insulated five sided box having an inner chamber, the box has an openable lid hingedly attached to the upper edge of the box;
   a temperature sensor in the inner chamber for detecting temperature readings of the inner chamber when the lid is closed;
   a peltier cooling element operably engaged to the inner chamber to remove heat;
   a voltage regulator operably connected to the sensor to change the cooling element in response to temperature readings from the sensor; and
   a wireless transmitter connected to the temperature sensor for transmission of temperature readings and detection of pre-determined temperatures.

2. The active cooler of claim 1 further comprising an AC charger for electrical power.

3. The active cooler of claim 1 further comprising a battery for supplying power to the cooler.

4. The active cooler of claim 1 further comprising a wireless transmitter operably engaged to the temperature sensor.

5. The active cooler of claim 1 further comprising a USB connector operably engaged to the voltage regulator.

6. An active cooler comprising:
   an insulated box having an insulated lid and an inner chamber;
   a temperature sensor in the inner chamber for detecting temperature readings of the inner chamber when the lid is closed and a memory for storing the temperature readings;
   a peltier cooling element operably engaged to the inner chamber to remove heat;
   a voltage regulator subunit operably connected to the sensor to change the cooling element in response the temperature readings from the sensor;
   a wireless transmitter connected to the memory for storing the temperature readings for transmission of the temperature readings; and
   a computer for processing data from the memory and detection of pre-determined temperatures.

7. The active cooler of claim 6 further comprising a toggle switch operably connected to the power source.

8. The active cooler of claim 6 further comprising a program that is operated by the computer to generate temperature and time related data.

9. The active cooler of claim 6 further comprising a signal transmitter to one of the following: cell phone, internet, or local area network to a third party user to retrieve temperature readings and warnings.

10. The active cooler of claim 6 further comprising a battery.

11. The active cooler of claim 10 wherein the battery is a lithium ion battery.

12. The active cooler of claim 6 wherein the lid locks upon engagement.

13. The active cooler of claim 6 further comprising an exhaust fan operably engaged to the inner chamber.

14. An active cooler comprising:
   an insulated container having an openable lid, the container having an inner chamber;
   a temperature sensor in the inner chamber for detecting temperature readings of the inner chamber when the lid is closed;
   a peltier cooling element operably engaged to the inner chamber to remove heat;
   a voltage regulator operably connected to the temperature sensor to change the cooling element in response to temperature readings from the sensor; and
   a wireless transmitter connected to the temperature sensor for transmission of temperature readings and detection of pre-determined temperatures.

15. The active cooler of claim 14 further comprising display mounted on the cooler.

16. The active cooler of claim 14 further comprising a fan for intake of air or expulsion of air with respect to the inner chamber.

17. The active cooler of claim 14 further comprising an alarm responsive to pre-determined temperature readings.

18. The active cooler of claim 14 further comprising a locking lid responsive to variance in temperatures outside desired parameters.

19. The active cooler of claim 17 further comprising transmission of a temperature reading to a hand held device by a wireless signal or through the internet.

20. The active cooler of claim 14 further comprising a memory for storage of predetermined temperatures and temperature readings from the inner chamber.

* * * * *